US008668703B2

(12) United States Patent
Sullivan et al.

(10) Patent No.: US 8,668,703 B2
(45) Date of Patent: Mar. 11, 2014

(54) MEDICAL DEVICES INCORPORATING COLLAGEN INHIBITORS

(75) Inventors: Christopher A. Sullivan, Winston-Salem, NC (US); Steve J. Hodges, Winston-Salem, NC (US); Anthony Atala, Winston-Salem, NC (US); James J. Yoo, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 430 days.

(21) Appl. No.: 11/948,294

(22) Filed: Nov. 30, 2007

(65) Prior Publication Data

US 2008/0132941 A1 Jun. 5, 2008

Related U.S. Application Data

(60) Provisional application No. 60/868,217, filed on Dec. 1, 2006.

(51) Int. Cl.
*A61B 17/10* (2006.01)
*A61B 17/04* (2006.01)
*A61L 17/00* (2006.01)

(52) U.S. Cl.
CPC .................. *A61B 17/04* (2013.01); *A61L 17/00* (2013.01); *Y10S 606/907* (2013.01)
USPC ........... 606/139; 606/151; 606/213; 606/907; 424/422; 424/443; 427/2.31

(58) Field of Classification Search
None
See application file for complete search history.

(56) References Cited

U.S. PATENT DOCUMENTS

| 4,291,687 A | 9/1981 | Sinnreich |
| 4,485,088 A | 11/1984 | Chvapil |
| 5,092,841 A | 3/1992 | Spears |
| 5,263,927 A | 11/1993 | Shlain |

(Continued)

FOREIGN PATENT DOCUMENTS

| WO | WO 98/23244 | 6/1998 |
| WO | WO 02/36054 A1 | 5/2002 |

(Continued)

OTHER PUBLICATIONS

"Palmoplantar pustulosis" from DermNetNZ pp. 1-2 (http://dermnetnz.org/scaly/palmoplantar-pustulosis.html) Sep. 2011.*

(Continued)

*Primary Examiner* — Bethany Barham
(74) *Attorney, Agent, or Firm* — Myers Bigel Sibley & Sajovec, P.A.

(57) ABSTRACT

Provided herein are implantable or insertable biomedical devices comprising a substrate and a collagen inhibitor on or in said substrate, and methods of treatment using the same. In some embodiments, the device is a urethral, ureteral, or nephroureteral catheter or stent. In some embodiments, the device is an absorbable esophageal or tracheal stent. Wound closure devices are also provided herein, including a substrate and a collagen inhibitor on or in the substrate. Also provided are surgical packings, including a substrate and a collagen inhibitor on or in the substrate. A barrier material for preventing adhesions in a subject is further provided, including a preformed or in situ formable barrier substrate and a collagen inhibitor on or in the substrate. Kits comprising the coated substrates are also provided.

33 Claims, 9 Drawing Sheets

(56) References Cited

U.S. PATENT DOCUMENTS

| | | | |
|---|---|---|---|
| 5,385,935 | A | 1/1995 | Tamai et al. |
| 5,449,678 | A | 9/1995 | Pines et al. |
| 5,564,439 | A | 10/1996 | Picha |
| 5,685,860 | A | 11/1997 | Chang et al. |
| 5,723,448 | A | 3/1998 | Gross et al. |
| 5,755,788 | A | 5/1998 | Strauss |
| 5,852,024 | A | 12/1998 | Pines et al. |
| 6,028,078 | A | 2/2000 | Hausheer et al. |
| 6,046,340 | A | 4/2000 | Seguin et al. |
| 6,063,396 | A * | 5/2000 | Kelleher ................. 424/428 |
| 6,090,814 | A | 7/2000 | Nagler et al. |
| 6,159,488 | A | 12/2000 | Nagler et al. |
| 6,224,630 | B1 | 5/2001 | Bao et al. |
| 6,239,177 | B1 | 5/2001 | Mori et al. |
| 6,281,262 | B1 * | 8/2001 | Shikinami ................. 523/105 |
| 6,328,994 | B1 | 12/2001 | Shimizu et al. |
| 6,376,543 | B1 | 4/2002 | Isaji et al. |
| 6,420,371 | B1 | 7/2002 | Pines et al. |
| 6,638,917 | B1 | 10/2003 | Li et al. |
| 7,025,753 | B2 | 4/2006 | Reever |
| 7,097,857 | B2 | 8/2006 | Tracy et al. |
| 7,135,197 | B2 | 11/2006 | Pena et al. |
| 7,189,410 | B1 * | 3/2007 | Drohan et al. ................. 424/447 |
| 2003/0108588 | A1 | 6/2003 | Chen et al. |
| 2003/0144727 | A1 * | 7/2003 | Rosenthal et al. ............ 623/1.15 |
| 2004/0043052 | A1 | 3/2004 | Hunter et al. |
| 2005/0038498 | A1 | 2/2005 | Dubrow et al. |
| 2005/0187609 | A1 | 8/2005 | Brar et al. |
| 2005/0208095 | A1 | 9/2005 | Hunter et al. |
| 2005/0220882 | A1 | 10/2005 | Pritchard et al. |
| 2005/0234538 | A1 | 10/2005 | Litvack et al. |
| 2006/0020331 | A1 * | 1/2006 | Bates et al. ................. 623/1.49 |
| 2006/0147492 | A1 | 7/2006 | Hunter et al. |
| 2006/0177480 | A1 | 8/2006 | Sung et al. |
| 2006/0204537 | A1 * | 9/2006 | Ratner et al. ................. 424/423 |
| 2006/0229711 | A1 | 10/2006 | Yan et al. |
| 2006/0293351 | A1 | 12/2006 | Pines et al. |
| 2007/0038291 | A1 | 2/2007 | Case et al. |
| 2007/0048351 | A1 | 3/2007 | Lunn |
| 2007/0142339 | A1 | 6/2007 | Whitehouse et al. |
| 2007/0148205 | A1 | 6/2007 | Whitehouse et al. |
| 2007/0160640 | A1 | 7/2007 | Jang et al. |
| 2007/0299409 | A1 | 12/2007 | Whitbourne et al. |
| 2008/0095819 | A1 * | 4/2008 | Gourdie et al. ............... 424/423 |
| 2008/0097580 | A1 | 4/2008 | Dave |
| 2008/0116106 | A1 * | 5/2008 | Lampropoulos et al. ..... 206/570 |
| 2009/0171317 | A1 | 7/2009 | Versi |
| 2009/0226500 | A1 | 9/2009 | Avelar et al. |
| 2010/0021519 | A1 | 1/2010 | Shenoy |

FOREIGN PATENT DOCUMENTS

| | | |
|---|---|---|
| WO | WO 02/087586 A1 | 11/2002 |
| WO | WO 2005/079703 A1 | 9/2005 |
| WO | WO 2005-112999 A2 | 12/2005 |
| WO | WO 2005-113031 A2 | 12/2005 |
| WO | WO 2006/107957 A2 | 10/2006 |
| WO | WO 2006/116989 A2 | 11/2006 |
| WO | WO 2007-084396 A2 | 7/2007 |

OTHER PUBLICATIONS

Nehls MC et al. Mithramycin Selectively inhibits collagen-α1(I) gene expression in human fibroblast. J. Clin. Invest. (Dec. 1993) 92: 2916-2921.

FDA Oncology Tools Product Label Details in Conventional Order for plicamycin, mithramycin. U.S. Food and Drug Administration. Supplemental No. 050109, 8 pp.

Bosher LH et al. The pathology of experimentally produced lye burns and strictures of the esophagus. The Journal of Thoracic Surgery. 1951: 483-489.

Burford TH et al. Caustic burns of the esophagus and their surgical management: a clinico-experimental correlation. Annals of Surgery. Sep. 1953; 139(3): 453-460.

McBride W et al. Restenosis after successful coronary angioplasty. The New England Journal of Medicine. Jun. 30, 1988; 318(26): 1734-1737.

Lindner V et al. Role of basic fibroblast growth factor in vascular lesion formation. Circulation Research. 1991; 68(1): 106-113.

Baskin LS et al. Biochemical characterization and quantitation of the collagenous components of urethral stricture tissue. The Journal of Urology. Aug. 1993; 150(2 Pt 2): 642-7 Abstract only.

Granot I et al. Halofuginone: an inhibitor of type I synthesis. Biochimica et Biophysica Acta. Feb. 13, 1993; 1156(2): 107-112 Abstract only.

Choi ET et al. Halofuginone, a specific collagen type I inhibitor, reduces anastomotic intimal hyperplasia. Arch Surg. Jun. 1995; 130(6): 257-261.

Nyska M et al. Topically applied halofuginone, an inhibitor of collagen type I transcription, reduces peritendinous fibrous adhesions following surgery. Connective Tissue Research. 1996; 34(2): 97-103 Abstract only.

Nagler A et al. Inhibition of collagen synthesis, smooth muscle cell proliferation, and injury-induced intimal hyperplasia by halofuginone. Arteriosclerosis, Thrombosis, and Vascular Biology. Jan. 1997;17(1):194-202 Abstract only.

Liu K et al. Halofuginone inhibits neointimal formation of cultured rat aorta in a concentration-dependent fashion in vitro. Heart Vessels. 1998; 13(1): 18-23 Abstract only.

Nagler A et al. The effect of halofuginone, an inhibitor of collagen type I synthesis, on urethral stricture formation: in vivo and in vitro study in a rat model. The Journal of Urology; Nov. 2000; 164(5): 1776-1780.

Regar E et al. Stent development and local drug delivery. British Medical Bulletin. 2001; 59: 227-48.

Da Silva FA et al. Extracellular matrix changes in urethral stricture disease. The Journal of Urology. Aug. 2002; 168: 805-807.

Finn AV et al. A novel rat model of carotid artery stenting for the understanding of restenosis in metabolic diseases. Journal of Vascular Research. 2002; 39: 414-426 (Marked copy).

Shargal Y et al. Inhibition of anastomotic intimal hyperplasia by a synthetic nonsulphated heparin-mimicking compound. Exp Clin Cardiol. Autumn 2002; 7(2/3): 73-79.

Arbell D et al. Prevention of esophageal strictures in a caustic burn model using halofuginone, an inhibitor of collagen type I synthesis. Laryngoscope 2005; 115(9): 1632-5 Abstract only.

Ferguson DD. Evaluation and management of benign esophageal strictures. Diseases of the Esophagus. 2005; 18: 359-364.

Mitra AK and Agrawal DK. In stent restenosis: bane of the stent era. J Clin Pathol. 2006; 59: 232-239.

Tierney W et al. Enteral stents. Technology Evaluation Report. Gastrointestinal Endoscopy. 2006; 63(7): 920-926.

Kopecki Z et al. Collagen loss and impaired wound healing is associated with c-Myb deficiency. Journal of Pathology. 2007; 211: 351-361.

Maluenda G et al. A critical appraisal of the safety and efficacy of drug-eluting stents. Clinical Pharmacology & Therapeutics. May 2009; 85(5): 474-480.

Leigh Perkins LE. Preclinical models of restenosis and their application in the evaluation of drug-eluting stent systems. Veterinary Pathology. Jan. 2010; 47(1): 58-76.

Schembre D. Advances in esophageal stenting: the evolution of fully covered stents for malignant and benign disease. Adv Ther. 2010: 27(7): 413-425.

Sharma P et al. Role of esophageal stents in benign and malignant diseases. The American Journal of Gastroenterology. Feb. 2010; 105: 258-273.

Coronary stent. Wikipedia. Retrieved Nov. 13, 2010: 1 p.
Foley catheter. Wikipedia. Retrieved Nov. 13, 2010: 3 pp.
Uteric stent. Wikipedia. Retrieved Nov. 13, 2010: 3 pp.
Wound healing. Wikipedia. Retrieved Nov. 13, 2010: 15 pp.
Stenosis. Wikipedia. Retrieved Jan. 18, 2011: 2 pp.
Extended European Search Report corresponding to European Application No. 07862365.9 dated Apr. 28, 2011.
Prausnitz MR et al. Current status and future potential of transdermal drug delivery. Nature Reviews. Feb. 2004; 3: 115-124.

(56) References Cited

OTHER PUBLICATIONS

Uhrich KE. Polymeric systems for controlled drug release. Chemical Reviews. 1999; 99(11): 3181-3198.
Edlund U and Albertsson A-C. Degradable polymer microspheres for controlled drug delivery. Advances in Polymer Science; 2002; 157: 67-112.
Gombotz WR and Pettit DK. Biodegradable polymers for protein and peptide drug delivery. Bioconjugate Chem. 1995; 6(4): 332-351.
Langer R. Biomaterials in drug delivery and tissue engineering: one laboratory's experience. Accounts of Chemical Research. 2000; 33(2): 94-101.
Langer R and Peppas NA. Advances in biomaterials, drug delivery, and bionanotechnology. AIChE Journal. Dec. 2003; 49(12): 2990-3006.
Angelova N and Hunkeler D. Rationalizing the design of polymeric biomaterials. Trends Biotechnol. 1999: 17(10): 409-421.
Griffith LG. Polymeric biomaterials. Acta Mater. 2000; 48: 263-277.
Office Action and Notice of Reference Cited (PTO-892), U.S. Appl. No. 12/130,657, mailed Sep. 6, 2013.
Office Action and Notice of Reference Cited (PTO-892), U.S. Appl. No. 12/130,614, mailed Sep. 9, 2013.
Office Action and Notice of Reference Cited (PTO-892), U.S. Appl. No. 11/948,335, mailed Sep. 10, 2013.
Nehls MC et al. Mithramycin Selectively inhibits collagen-$\alpha$1 (I) gene expression in human fibroblast. J. Clin. Invest. (Dec. 1993) 92: 2916-2921.
*Retraction of:* [Nehls MC et al. Mithramycin Selectively inhibits collagen-$\alpha$1(I) gene expression in human fibroblast. J. Clin. Invest. (Dec. 1993) 92: 2916-2921] J. Clin. Invest. (Oct. 2003) 112(8): 1265.
Yamada H. et al. Tranilast, a selective inhibitor of collagen synthesis in human skin fibroblasts. J. Biochem. (Oct. 1994) 116(4): 892-897, Abstract only.
Chen S-J et al. Mithramycin inhibits myointimal proliferation after balloon injury of the rat carotid artery in vivo. Circulation (Nov. 1994) 90(5): 2468-73.
Nagler A. et al. Halofuginone—an inhibitor of collagen type I synthesis—prevents postoperative formation of abdominal adhesions. Annals of Surgery (1998) 227(4): 575-582.
Fishbein I et al. Local delivery of mithramycin restores vascular reactivity and inhibits neointimal formation in injured arteries and vascular grafts. Journal of Controlled Release (2001) 77: 167-181.
Sandorfi N. et al. Inhibition of collagen gene expression in systemic sclerosis dermal fibroblasts by mithramycin. Ann Rheum Dis (2005) 64: 1685-1691.
Tanaka et al. Newly developed biodegradable stents for benign gastrointestinal tract stenosis: a preliminary clinical trial. Digestion (Mar. 6, 2006) 74: 199-205.
FDA Oncology Tools Product Label Details in Conventional Order for plicamycin, mithramycin. U.S. Food and Drug Administration. Supplemental No. 050109, 8 pp. retrieved online May 30, 2008.
International Search Report and Written Opinion, PCT/US07/024615, mailed Apr. 3, 2008.

* cited by examiner

MEDICAL DEVICES INCORPORATING COLLAGEN INHIBITORS

RELATED APPLICATIONS

This application claims the benefit of U.S. Provisional Patent Application Ser. No. 60/868,217, filed Dec. 1, 2006, the disclosure of which is incorporated by reference herein in its entirety.

FIELD OF THE INVENTION

The present invention concerns medical devices, including implantable devices such as catheters and stents, as well as wound closure devices such as staples and sutures.

BACKGROUND OF THE INVENTION

Scar tissue forms in response to tissue injury after trauma. This response is mediated by multiple inflammatory pathways and involves the development of a complex matrix of collagen, hyaluronic acid, fibronectin, and proteoglycans (Salamone et al. *Current Otolaryngology*. McGraw Hill, 2006). Though relatively expedient, healing by scar tissue deposition (cicatrization) does not replace functional tissue by multi-germ layer regeneration.

Forty-five million surgeries are performed annually in the United States, and with every surgery there is inevitable formation of scar tissue (DeFrances et al. *Advance Data From Vital and Health Statistics*. 2006 May; 371: 14). Fibrous adhesion formation after surgery or other trauma to tubular structures such as the esophagus, tracheobronchial tree, ureter, fallopian tubes and gut can lead to chronic illness and death. Scar tissue that forms in muscle, bone and skin tissue may lead to chronic orthopedic conditions, chronic pain, cosmetic deformity and decreased quality of life.

An example is paranasal sinus surgery. The paranasal sinuses are air spaces in the mammalian facial skeleton. These spaces can become obstructed due to various conditions such as allergy, infection, tumor, and radiation therapy. When conventional medical therapy fails, paranasal sinus surgery is a common procedure used to establish sinus drainage and to relieve the symptoms of sinus obstruction. Nearly 200,000 chronic sinus disease patients undergo sinus surgery that fails in more than 50% of cases due to unfavorable scar formation (Musy et al. *American Journal of Otolaryngology*. 2004 November-December; 25(6):418-22). Revision surgery has a higher complication rate than initial surgery, is less successful, and is associated with a perceived decrease in quality of life (Jiang et al. *Annals of Otology, Rhinology, and Laryngology*. 2002 February; 11(2):155-59).

Attempts to decrease scar tissue formation during wound healing such as with anti-inflammatory agents and inhibitors of fibroblast proliferation, are indirect and largely ineffective. These agents are non-specific, and not only inhibit fibroblasts, but also inhibit epithelial cell migration. In paranasal sinus surgery in particular, a cavity is created that must re-epithelialize with functional sinus lining (mucosa) that will promote active mucociliary clearance of sinus debris; therefore agents that inhibit re-epithelialization are counter productive to optimal healing in the paranasal sinus.

There is need for new approaches that will specifically target scar tissue without inhibiting germ layer regenerative tissue processes in order to alleviate scar tissue formation and other problems associated with medical interventions.

SUMMARY OF THE INVENTION

Provided herein are implantable or insertable biomedical devices comprising a substrate and a collagen inhibitor on or in said substrate. In some embodiments, the substrate includes a material selected from the group consisting of vinyl, polyethylene, poly(vinyl chloride) (PVC), ethylene vinyl acetate (EVA), silicone, latex, and polypropylene. In some embodiments, the collagen inhibitor is selected from the group consisting of: mithramycin, mitomycin-c, tranilast, halofuginone and analogs thereof.

Wound closure devices are also provided herein, including a substrate and a collagen inhibitor on or in the substrate. In some embodiments, the substrate is selected from the group consisting of biodegradable substrates and non-biodegradable (inert) substrates. In some embodiments, the device is a suture, staple, tape, or bandage. In some embodiments, the substrate includes a biodegradable polymer, e.g., poly(lactide)s, poly(glycolide)s, poly(lactide-coglycolide)s, poly(lactic acid)s, poly(glycolic acid)s, poly(lactic acid-co-glycolic acid)s, poly(caprolactone), polycarbonates, polyesteramides, polyanhydrides, poly(amino acid)s, poly(ortho ester)s, polycyanoacrylates, polyamides, polyacetals, poly(ether ester)s, copolymers of poly(ethylene glycol) and poly(ortho ester)s, poly(dioxanone)s, poly(alkylene alkylate)s, biodegradable polyurethanes, blends and copolymers thereof, etc. In some embodiments, the substrate is a suture formed of braided, woven, or non-woven fiber material, e.g., silk, cotton, rayon, linen, wool, satin, nylon, polyester, polypropylene, polytetrafluoroethylene or combinations thereof. In some embodiments, the collagen inhibitor is selected from the group consisting of: mithramycin, mitomycin-c, tranilast, halofuginone and analogs thereof.

Also provided are surgical packings (e.g., sinus packings), including a substrate and a collagen inhibitor on or in the substrate. In some embodiments, the substrate includes a material selected from the group consisting of oxycellulose, methylcellulose, hydroxypropylmethylcellulose, hydroxybutylmethylcellulose, hydroxyethylmethylcellulose, ethylhydroxyethylcellulose, hydroxyethylcellulose, hydroxypropylcellulose, carboxymethylcellulose, microcrystalline cellulose, xanthan gum, silicon dioxide, and mixtures thereof. In some embodiments, the substrate is in the form of a dry powder. In some embodiments, the collagen inhibitor is selected from the group consisting of: mithramycin, mitomycin-c, tranilast, halofuginone and analogs thereof.

Methods of treating a paranasal sinus wound in a subject in need thereof are provided, including topically administering a collagen inhibitor in an amount effective to treat said wound. In some embodiments, the administering step is carried out by packing the paranasal sinus with a sinus packing material (e.g., a cellulose compound or gel) that includes a collagen inhibitor. In some embodiments, the collagen inhibitor is selected from the group consisting of: mithramycin, mitomycin-c, tranilast, halofuginone and analogs thereof.

Methods of treating esophageal or tracheal stricture in a subject in need thereof are also provided, comprising topically administering a collagen inhibitor in an amount effective to treat the stricture in the subject. In some embodiments, the administering step is carried out by stenting the stricture with a biodegradable stent comprising said collage inhibitor. In some embodiments, the collagen inhibitor is selected from the group consisting of: mithramycin, mitomycin-c, tranilast, halofuginone and analogs thereof.

A barrier material for preventing adhesions in a subject is further provided, including a preformed or in situ formable barrier substrate and a collagen inhibitor on or in the substrate. In some embodiments, the collagen inhibitor is selected from the group consisting of: mithramycin, mitomycin-c, tranilast, halofuginone and analogs thereof.

Methods of treating abdominal adhesions in a subject in need thereof are provided, including topically administering into the abdominal cavity of the subject a collagen inhibitor in an amount effective to treat said abdominal adhesions in said subject. In some embodiments, the collagen inhibitor is selected from the group consisting of: mithramycin, mitomycin-c, tranilast, halofuginone and analogs thereof.

Kits including the implantable or insertable biomedical devices are also provided.

The present invention is explained in greater detail in the specification set forth below.

DETAILED DESCRIPTION OF THE PREFERRED EMBODIMENTS

The disclosures of all United States Patent references cited herein are to be incorporated by reference herein as if fully set forth.

Figure 1:
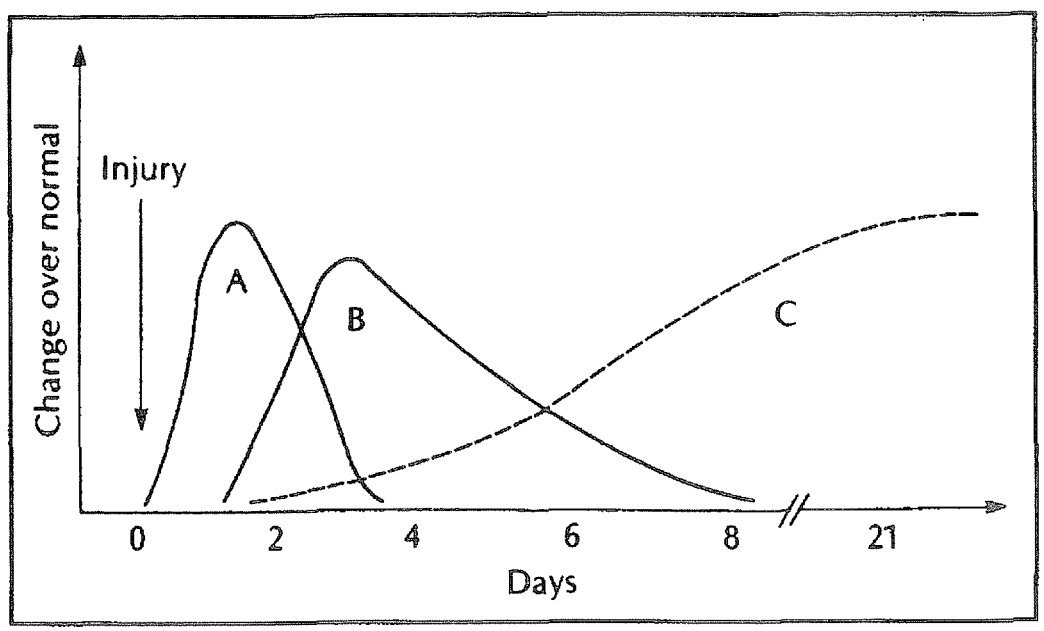
FIG. 1. Schematic diagram of the three phases of wound healing. A: Inflammation, B: Fibroplasia, C: Maturation FIG. 2. Scanning electron microscopy of HF—Br coated 3-0 Vicryl sutures (A) and uncoated 3-0 Vicryl sutures (B) at 200× magnification.

Healing through the deposition of scar (fibrous) tissue is the normal response to injury. In humans, the wound healing response is divided into three phases: inflammation, fibroplasias and maturation. The steps of the process overlap broadly and are best understood as a continuum rather than a series of discrete steps (FIG. 1).

Without wishing to be bound to any particular theory, the wound healing process begins with a disturbance of blood vessel integrity that exposes the subendothelial collagen to blood platelets. This event is the initiating step that leads to blood extravasation and triggers the acute inflammatory response. This response activates local and systemic factors that lead to an orderly and predictable migration of cells into the wound. The first cells to appear in the wound are neutrophils, followed by monocytes and fibroblasts. Fibroblasts are the dominant cell type during fibroplasia. This phase is characterized by fibroblast proliferation and migration. The major function of the fibroblast during this stage is to elaborate interstitial matrix and collagen type-1. It is this collagen that makes up the fibrous tissue that characterizes the clinical entity referred to as scar tissue. When the fibroplasia stage is complete, the final stage of maturation occurs during which the wound becomes acellular and undergoes remodeling over months to years. During the remodeling phase the wound gathers tensile strength. Under the influence of various mediators and enzymes, remodeling is thought to represent the interplay between matrix synthesis and degradation.

Provided herein are compositions, devices and methods of treatment to improve wound healing after medical procedures such as surgery or other trauma. In some embodiments, the present invention provides collagen inhibitors topically administered to the wound or site of injury. "Stenosis" or "stricture" refers to the narrowing of a bodily canal, passageway or tubular structure or organ.

"Subjects" that may be treated by the present invention include both human subjects for medical purposes and animal subjects for veterinary and laboratory purposes. Other suitable animal subjects are, in general, mammalian subjects such as primates, bovines, ovines, caprines, porcines, equines, felines, canines, lagomorphs, rodents (e.g., rats and mice), etc. Human subjects are the most preferred. Human subjects include fetal, neonatal, infant, juvenile, adult and geriatric subjects.

"Treat" as used herein refers to any type of treatment or prevention that imparts a benefit to a subject afflicted with or at risk of developing scarring or complications involving scar tissue production and/or collagen production, including improvement in the condition of the subject (e.g., in one or more symptoms), delay in the progression of the scarring, delay the onset of symptoms or slow the progression of symptoms, etc. As such, the term "treatment" also includes prophylactic treatment of the subject to prevent the onset of symptoms. As used herein, "treatment" and "prevention" are not necessarily meant to imply cure or complete abolition of symptoms, but refer to any type of treatment that imparts a benefit to a patient afflicted with a disease, including improvement in the condition of the patient (e.g., in one or more symptoms), delay in the progression of the disease, etc.

"Treatment effective amount", "amount effective to treat" or the like as used herein means an amount of the collagen inhibitor sufficient to produce a desirable effect upon a patient inflicted with wounds or site of injury. This includes improvement in the condition of the patient (e.g., in one or more symptoms), delay in the progression of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

1. Collagen Inhibitors

"Collagen inhibitors" useful for carrying out the present invention are known and include all agents that inhibit the synthesis of collagen. See, e.g., U.S. Pat. Nos. 6,046,340 and 5,092,841; PCT Publication No. WO/2005/112999. Collagen is the major protein component of the extracellular matrix in organisms. There are at least 12 types of collagens, with types I, II and III being the most common. They are primarily synthesized in the body by fibroblasts during healing, and are formed by processing of the precursor procollagen proteins.

In some embodiments, inhibitors of type-1 collagen (also known as type I collagen) are preferred. The primary component of scar tissue, collagen type-1 alpha, typically forms a protein rod 300 nm long composed of 3 subunits: two α1(I) chains and one α2(I) chain. Within the fibroblast, elaboration of type-1 collagen is controlled by activation of the alpha-1 collagen gene. Therefore, in some embodiments, inhibitors of the alpha-1 collagen gene expression are preferred.

Examples of "collagen inhibitors" as used herein include, but are not limited to, mithramycin, mitomycin-c, tranilast, halofuginone, d-penicillamine, beta-aminopropionitrile, okadaic acid, LY294002 (PI-3K inhibitor), 5-fluorouracil, analogs thereof, etc.

Mithramycin (MIT or plicamycin) is an aureolic acid polyketide antibiotic that binds to GC-rich areas of DNA, and is typically used as a chemotherapeutic agent. See, e.g., U.S. Pat. No. 5,723,448. Mitomycin-c is a known fibroblast inhibitor with known scar inhibitory effects in the eye, sinus and trachea.

Tranilast (2-(2,3-dimethoxycinnamoyl)aminobenzoic acid) is also known and described in, for example, U.S. Pat. Nos. 5,385,935; 6,239,177; and 6,376,543.

"Halofuginone" or halofuginone bromide (7-bromo-6-chloro-3-[3-(3-hydroxy-2-piperidinyl)-2-oxopropyl]-4(3H) is known and described in, for example, U.S. Pat. Nos. 5,449,678, 6,420,371; 6,028,078; 6,090,814; and 6,159,488. Halofuginone is a quinazolinone compound that has been used in the cattle and poultry industries as an anti-coccidal agent. Serendipitously, it was discovered that dermal thinning was occurring in chickens that were administered the drug systemically. Further study of this phenomenon led to the discovery that the mechanism of action of halofuginone was inhibition of the alpha-1 collagen gene promoter (Granot I et al. Poult Sci. 1991 July; 70(7):1559-63). The pharmacology of this compound has been extensively studied for veterinary use and has FDA orphan drug approval for use in humans to treat scleroderma.

II. Substrates

Substrates include any biocompatible substrate, and may be biodegradable or non-biodegradable.

Biodegradable or bioabsorbable substrates may be formed of biodegradable polymers. Any suitable polymer may be employed, including, but not limited to, poly(lactide)s, poly(glycolide)s, poly(lactide-coglycolide)s, poly(lactic acid)s, poly(glycolic acid)s, poly(lactic acid-co-glycolic acid)s, poly(caprolactone), polycarbonates, polyesteramides, polyanhydrides, poly(amino acid)s, poly(ortho ester)s, polycyanoacrylates, polyamides, polyacetals, poly(ether ester)s, copolymers of poly(ethylene glycol) and poly(ortho ester)s, poly(dioxanone)s, poly(alkylene alkylate)s, biodegradable polyurethanes, as well as blends and copolymers thereof. See, e.g., U.S. Pat. No. 7,097,857.

According to some embodiments, the present invention provides a wound closure device comprising a substrate and a collagen inhibitor on or in said substrate. The substrate may comprise, consist of or consist essentially of a biodegradable substrate (such as albumin, collagen, synthetic polyamino acids, prolamines, polysaccharides, etc., or biodegradable polymers such as polylactides, polyglycolic acids, poly(lactide-co-glycolides), polycaprolactones, polycarbonates, polyamides, polyanhydrides, polyamino acids, polyortho esters, polyacetals, polycyanoacrylates, and degradable polyurethanes) or a non-biodegradable (inert) substrates such as silicone and silk, or polyvinyl alcohol, polyethylene, polyurethane, polypropylene, polycaprolactone, polyacrylates, ethylene-vinyl acetates, polystyrenes, polyvinyl oxides, polyvinyl fluorides, poly(vinyl imidazoles), chlorosulphonated polyolefins, polyethylene oxides, polytetrafluoroethylenes, nylons, and copolymers and combinations thereof. The device may take any suitable form, such as a suture, staple, tape, or bandage. In some embodiments the collagen inhibitor is carried in a biodegradable polymer which is coated on an inert or non-biodegradable substrate.

In some embodiments the device is a suture. Sutures may be formed of biodegradable polymers as described above (which may be in the form of a unitary solid), or may be formed from braided, woven, or non-woven fiber material (e.g., silk, cotton, rayon, linen, wool, satin, nylon, polyester or mixtures thereof). See, e.g., U.S. Pat. Nos. 5,685,860 and 6,224,630. In some embodiments, sutures include polypropylene (e.g., prolene or marlex) and/or polytetrafluoroethylene (PTFE) (e.g., Gore-Tex).

The present invention also provides surgical packings (e.g., sinus packings) that include a substrate and a collagen inhibitor on or in said substrate. The packing may take any suitable form, including, but not limited to, those described in U.S. Pat. Nos. 5,263,927 and 4,291,687.

The substrate material for the packing may be formed of any suitable material, including but not limited to methylcellulose, hydroxypropylmethylcellulose, hydroxybutylmethylcellulose, hydroxyethylmethylcellulose, ethylhydroxyethylcellulose, hydroxyethylcellulose, hydroxypropylcellulose, carboxyethylcellulose, microcrystalline cellulose, xanthan gum, silicon dioxide, and mixtures thereof. See, e.g., U.S. Pat. No. 7,135,197. Oxycellulose is currently used as a wound packing to achieve hemostatis. In some embodiments the substrate may be provided in the form of a dry, preferably sterile, powder (e.g., with which the collagen inhibitor may be mixed).

In some embodiments, a barrier material is used for preventing adhesions in a subject, comprising in combination, a preformed or in situ formable barrier substrate and a collagen inhibitor on or in said substrate. The substrate may be any suitable material, and when formed in situ any suitable crosslinking agent may be employed. Suitable examples include but are not limited to those described in U.S. Pat. No. 6,638,917. The substrate or material may be bioabsorbable (e.g., a hemostatic material) or non-bioabsorbable (e.g., a non-absorbable mesh, such as is currently used in hernia repair).

A further aspect of the invention is an implantable or insertable biomedical device comprising a substrate and a collagen inhibitor on or in said substrate. In some embodiments, the device is a urethral, ureteral, or nephroureteral catheter or stent. Various nasal, esophageal and tracheal stents are also known. Cranial, maxillary and mandibular bone plates include bioabsorbable substrates (such as poly-L-lactic-polyglycolic plates (PLLA/PGA)) and non-bioabsorbable substrates (such as titanium).

In some embodiments, a non-bioabsorbable stent (i.e., a tube designed to prevent luminal strictures) anywhere in the body. Examples include, but are not limited to, Urethral catheter, Ureteral stent, Nephroureteral catheter, Esophageal stent, Tracheostomy stent, Gastric feeding tube, Nasogastric tube, Laryngeal/tracheal/pulmonary stent, Myringotomy tube, Nasal stent, Salivary duct stent, Biliary stent, Enteric stents, Nasolacrimal stents.

Still other examples are described below. The substrate may be comprised of any suitable biodegradable or non-biodegradable material. In some embodiments the substrate (e.g., from which the catheter is formed) comprises a material such as vinyl, polyethylene, poly(vinyl chloride) (PVC), ethylene vinyl acetate (EVA), silicone, latex, or polypropylene.

See, e.g., U.S. Pat. No. 7,025,753. The collagen inhibitor may be coated on such a substrate material, with or without a carrier (such as a biodegradable polymer), by any suitable technique as discussed further below.

Specific examples of devices or products that can be used to carry out the present invention by including a collagen inhibitor on or in a substrate from which the product or device is formed include, but are not limited to (for various fields):

Urology:
Coated Urethral Catheter
Coated Ureteral Stent
Coated Nephroureteral Catheter
Ent:
Coated Sinus Packing Material
Injectable sinus packing material
Coated Esophageal Stent
Coated Tracheostomy Tube
Coated Gastric Feeding Tube
Coated Nasogastric Tube
Coated Laryngeal/Tracheal/Pulmonary Stent
Injectable Material for Vocal Fold Augmentation
Coated Myringotomy Tube
Coated Nasal Septal Splint
Coated Nasal Stent
Coated Salivary Duct Stent
Coated Laryngeal Implant
Injectable gel for salivary radiation fibrosis
Coated cranial, maxillary, mandibular absorbable and nonabsorbable bone plates
Plastic Surgery/Dermatology:
Coated Silicone Implants (or Coated Implants of other Composition)
Injectable Material for Cosmetic Augmentation (Bulking Agent)
Cream/Gel/Spray for Prevention of Hypertrophic Scar
Coated Silicone Sheets for the Prevention of Scarring
Cream/Gel/Spray/Silicone Sheets to Prevent Burn Scarring/Contractures
Coated skin graft material
Coated Suture for Wound Closure
Coated Skin Staples/Intracorporeal Staples
Coated "Steri-Strips" Wound Closure Adhesives
General Surgery:
Coated Sheets or Sprays for the Prevention of Surgical Adhesions
Coated Biliary Stents
Coated Enteric Stents
Ophthalmology
Coated Nasolacrimal Stents
Vascular Surgery:
Coated Endovascular Stents
Cardiology:
Coated Endovascular Cardiac Stents
Orthopaedic:
Coated absorbable and nonabsorbable bone plates
Miscellaneous:
Coating for other Implanted Artificial Medical Devices (vascular access devices, insulin pumps, etc)
Coated synthetic polymers [e.g., polyglycolic acid (PGA), polylactic acid (PLA), and poly(lactic-co-glycolic acid) (PLGA)], used to make absorbable vascular stent, cardiovascular stents, staples, suture Devices, materials, and compositions of the invention may be used in the treatment of both human subjects and animal subjects such as dogs, cats, horses, cattle, sheep, monkeys, etc. for veterinary or laboratory purposes.

III. Formulations

In some embodiments, collagen inhibitors of the present invention are provided as a coating on a substrate. Collagen inhibitors may be coated on a substrate by any suitable technique, such as dipping, spraying, spray drying, etc. The collagen inhibitor may be applied per se or concurrently with a carrier material or film-forming material, such as a biodegradable polymer (e.g., as described above). Collagen inhibitors may be combined into materials (such as powders or biodegradable materials) by any suitable technique, such as mixing, co-extruding, etc. In some embodiments, the collagen inhibitor is included in an amount effective to inhibit scar formation and/or collagen formation on or adjacent the implanted or inserted substrate.

According to some embodiments, for suture and/or packing materials the coating process includes one or more of the following steps: (a) prepare materials to desired size and shape for implantation; (b) prepare a solution of a collagen inhibitor (e.g., HFBr at 0.5 µg/ml); (c) materials are then dipped and immediately frozen at −80F for approximately 24 hours; (d) Frozen materials are then lyophilized (i.e., vacuum dried); (e) materials are sterilized, e.g., using ethylene oxide or gamma irradiation.

According to some embodiments, coating and/or impregnating stent materials (e.g., for esophagus, trachea, vascular, etc.) with a collagen inhibitor includes one or more of the following steps: (a) dry collagen inhibitor (e.g., HFBr) in powder form is mixed (e.g., in a 50:50 ratio) with stent material also in powder form (e.g., PLLA, PGA, Vicryl (polygalactin)); (b) powder material is then electrospun into desired shape (in some embodiments, this process results in a collagen inhibitor impregnated stent that allows freedom to make the desired shape for implantation); (c) stent is sterilized, e.g., using ethylene oxide or gamma irradiation.

According to some embodiments, wound glue including a collagen inhibitor includes one or more of the following steps: (a) the collagen inhibitor (e.g., HFBr at 0.5 µg/ml) is mixed 50:50 with a suitable glue material (e.g., acrylate material); and (b) applied directly to the wound.

According to some embodiments, coating of stents (e.g., permanent catheters) with a collagen inhibitor includes one or more of the following steps. (a) Weigh stent; (b) Modify surface of the stent with a plasma reactor, or alternatively microwave water wet stent for about 30-60 seconds; (c) Immerse stent in collagen inhibitor (e.g., halofuginone) and freeze in liquid nitrogen or −80C); (d) Lyophilize stent (e.g., overnight); (e) Weigh stent; (f) Immerse stent in 1% PEG (3500-5000 g/mol filtered in 0.2 um filter); (g) Freeze PEG in liquid nitrogen or −80C, and lyophilize overnight; (h) Immerse stent in collagen inhibitor (e.g., halofuginone) and freeze and lyophilize overnight; (i) Weigh stent; and (j) Sterilize.

According to some embodiments, coating of stents (e.g., permanent catheters) with a collagen inhibitor includes one or more of the following steps. (a) Weigh stent (b) Modify surface of the stent with a plasma reactor, or alternatively microwave wet stent (e.g., wet with PBS and covered with PBS soaked gauze) for about 30-60 seconds; (c) Dip stent in 2% PLGA-COOH to cool; (d) Dry under hood; (e) Cover with soaked gauze (e.g., with PBS) and microwave for about 30-60 seconds (or use plasma reactor); (f) Coat stent with halofuginone (e.g., immerse) and freeze in liquid nitrogen and lyophilize overnight; (g) Weight stent to estimate drug content; and (h) Sterilize.

Those of skill in the art will appreciate that all of the above methods can be modified and optimized as desired by routine methods without departing from the spirit of the invention disclosed herein.

IV. Dosages and Routes of Administration

In preferred embodiments, collagen inhibitors of the present invention are administered topically (i.e., locally) to the wound or site of injury. In some embodiments, compositions including collagen inhibitors may be administered via a coated suture, via combination with a gel or suitable wound glue, via coatings and/or impregnating collagen inhibitors onto a suitable substrate as described herein.

In some embodiments, topical application of one or more collagen inhibitors in nano ($10^{-9}$) or pico ($10^{-12}$) molar doses is sufficient to inhibit collagen type-1 production in an open wound. In some embodiments, collagen inhibitors is used topically as a packing material (e.g., in the sinus after paranasal sinus surgery) to prevent post-operative scar tissue formation.

In some embodiments, collagen inhibitors are administered by elution/absorption of the drug in less than 30 minutes. In some embodiments, administration is performed over a longer period of time, e.g., substantial elution over 30 minutes, 1, 2 or 3 hours, and up to 5, 6, 7 or 8 days. In some embodiments, collagen inhibitors are eluted over time to capture as much of the early fibroplasia stage of wound healing as possible (e.g., over 3-7 days).

In some embodiments, HF is administered in a single or total dosage over time of 0.5, 1.0 or 1.5 to 2.0, 2.5, 3.0, 3.5 or 4.0 mg/kg. In some embodiments, the total dosage is 0.5 to 10 mg. In some embodiments, HF is administered in nano ($10^{-9}$) or pico ($10^{-12}$) molar doses.

Some embodiments of present invention are explained in greater detail in the following non-limiting examples.

EXAMPLES

Example 1

Effect of a Collagen Type-1 Inhibitor on Dermal Wound Healing

Halofuginone has been used in experimental animal models as a systemic agent to inhibit scar formation (Pines et al. *General Pharmacology*, 1998 April; 30(4):445-50; Pines et al. *Biol Blood Marrow Transplant.* 2003 July; 9(7):417-25). However, little is know about its effectiveness as a topical agent for this purpose.

Experimental models for wound healing and scar tissue formation are well described in the rat, and all incorporate dorsal skin incisions (Kapoor et al. *The American Journal of Pathology.* 2004; 165:299-307). The rat has a relatively thick dermis on the dorsum that approximates the thickness of human dermis.

A total of nine animals underwent surgery: three controls and six treatment animals. On each control animal four full thickness dermal incisions were made on the dorsum. The two anterior incisions were closed with uncoated 3-0 Vicryl and N-butyl-2-cyanoacrylate glue; the posterior incisions were closed with Vicryl alone. In the experimental animals four full thickness wounds were made on the dorsum; the two anterior incisions were closed uncoated Vicryl and a mixture of HF—Br and N-butyl-2-cyanoacrylate (0.5 cc of HF—Br was added to 0.5 cc of N-butyl cyanoacrylate glue) was applied topically to the closed wound. The two posterior wounds were closed with HF—Br coated 3-0 Vicryl. Two treatment animals and one control animal were then euthanized at 2, 6, and 12 weeks and soft tissue specimens were taken for analysis.

Figure 2:
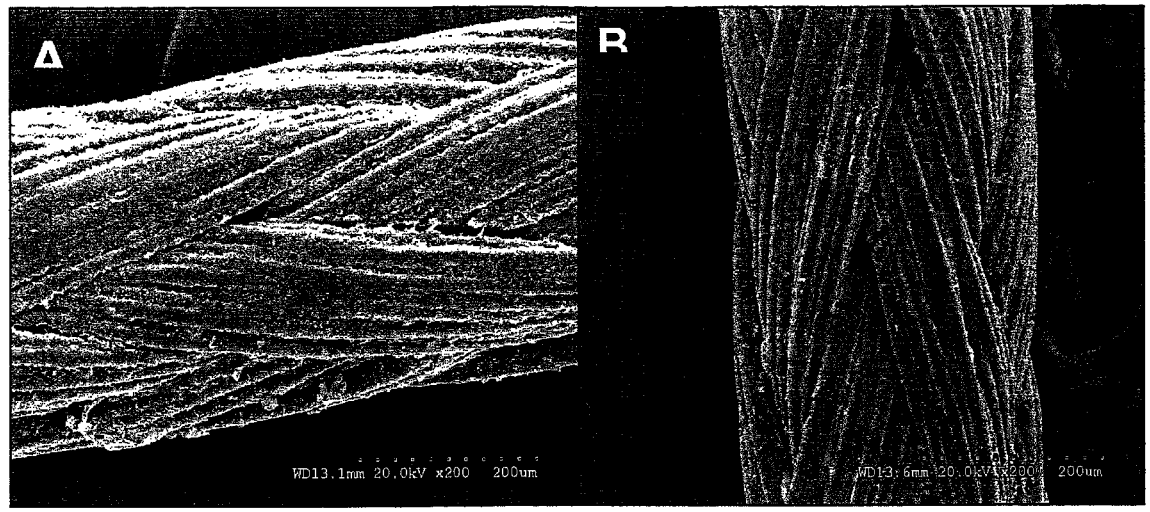

Suture Coating: 3-0 Vicryl absorbable sutures were weighed and placed in 1 ml serological pipettes. The pipettes were then filled with Ice of Halocur™ Halofuginone Bromide 0.5 mg/ml (Halocur® (Oral Halofuginone. 0.5 mg/mL) from Intervet International BV of Norway) and frozen at −80° C. for 24 hours and lyophilized. Pre and post coating weights were recorded and scanning electron microscopy (SEM) was used to show drug coating (particulate matter) on sutures (FIG. 2). Visual inspection of the coated sutures demonstrated a yellow coating, providing further evidence that the yellow Halocur had adhered.

Sutures were sterilized in ethylene oxide for surgical use. Weight recordings taken before and after coating showed an average of 96 μg/cm of drug on coated sutures.

Figure 3:
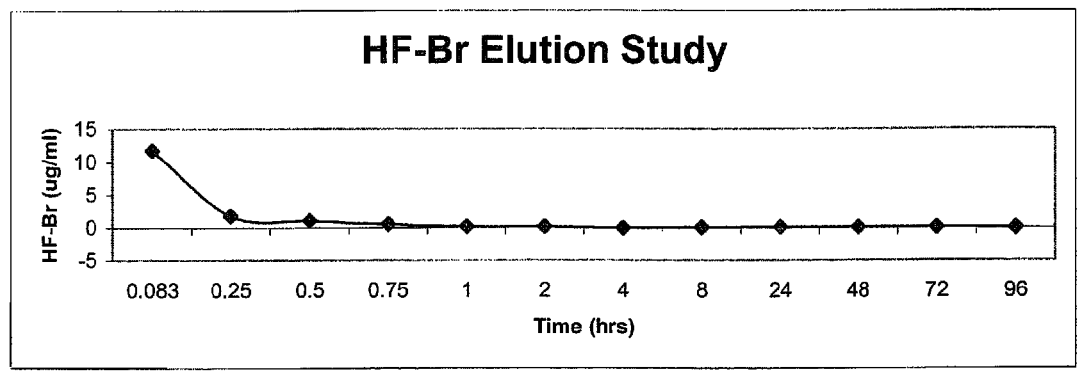
FIG. 3. Elution of HF—Br in vitro shows rapid drug release detected by UV spectroscopy at 243 nm.

To determine halofuginone elution, an in vitro elution study was performed. The release of halofuginone from coated Vicryl sutures into phosphate buffered saline (PBS) was used to estimate kinetics of drug release in vivo. A 2.5 cm segment of HF—Br coated Vicryl was placed in 1.5 mL of PBS and incubated at 37° C. At 5, 15, 30, and 45 minutes and 1, 2, 4, 8, 24, 48, 72, and 96 hours the segment was transferred into a new 1.5 mL aliquot of PBS, and the amount of halofuginone from the previous aliquot was measured with UV spectrophotometry at 243 nm. Data from UV spectrophotometry indicated a rapid release of HF—Br into PBS in vitro (FIG. 3). It was approximated that 90% of the total drug mass was released in 30 minutes and that the drug was nearly eliminated in 2 hours.

Gross Appearance of Wounds: More erythema and induration were visible in control wounds at two weeks than HF—Br treated wounds (data not shown). No significant difference in appearance was visible at later time points.

Figure 4A:
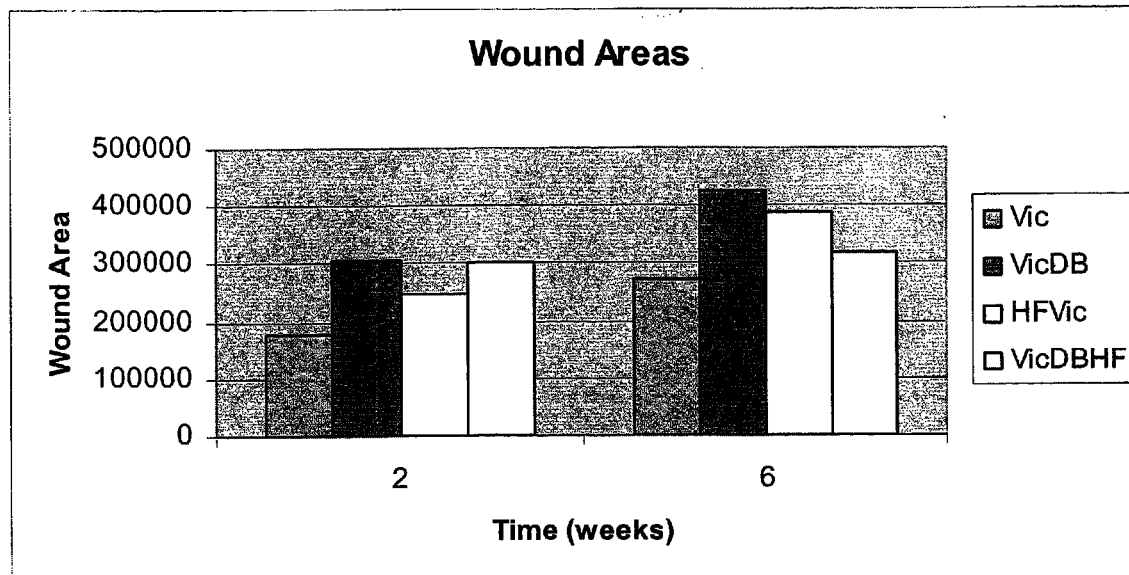
FIG. 4. Histology results. 4A: Wound Areas. 4B: Fibroblast Counts. Vic: uncoated 3-0 Vicryl suture. VicNBC: uncoated 3-0 Vicryl suture; then N-butyl-2-cyanoacrylate glue applied topically. HFVic: 3-0 Vicryl suture coated with halofuginone bromide. VicNBCHF: uncoated 3-0 Vicryl suture; then mixture of N-butyl-2-cyanoacrylate glue and halofuginone bromide applied topically. HF—Br: Halofuginone Bromide.
Figure 4B:
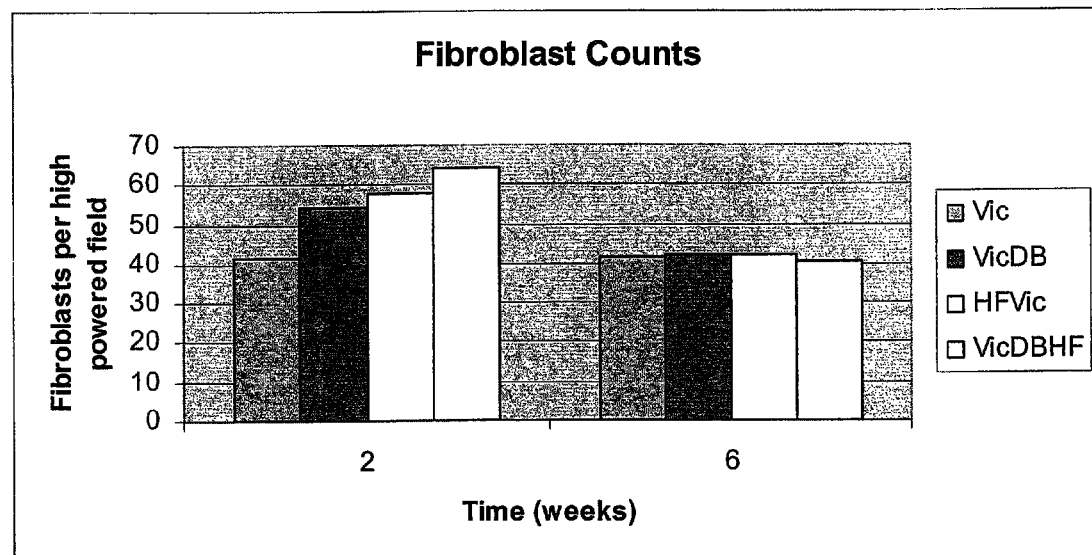

Soft tissue samples were harvested, embedded in paraffin and sectioned (5 μm). Sections were stained with Hematoxylin and Eosin (H&E) and Masson's Trichrome. Inflammation scores were recorded according to the method of Storch (*Surgical Infections.* 2002; 3: 89-98). The area of scar tissue deposition was approximated and calculated with light microscopy and a ZeiSS™ digital image capture software system. Results are shown in FIG. 4.

Figure 5A:
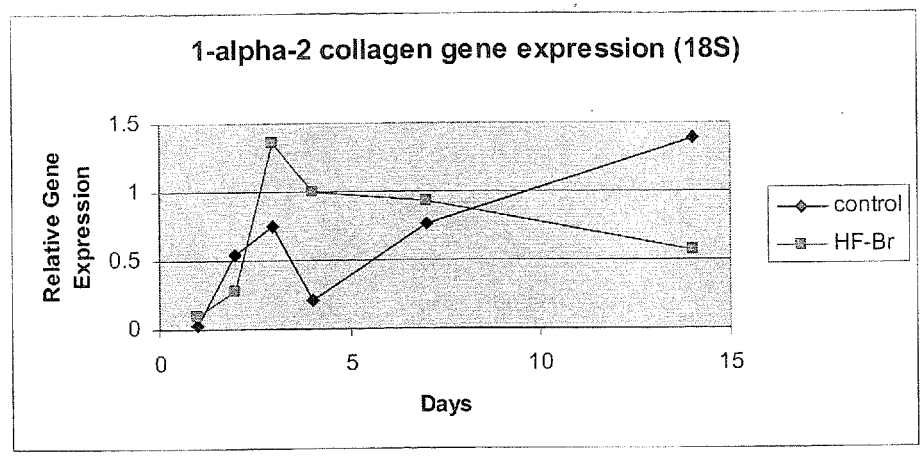
FIG. 5. Alpha 1 Collagen Gene Expression. Relative quantities of alpha 1 collagen gene expression were normalized with expression levels of 18 S (5A) and GAPDH (5B) RNA. These values were then divided by the relative quantity of alpha 1 collagen gene expression in normal skin.
Figure 5B:
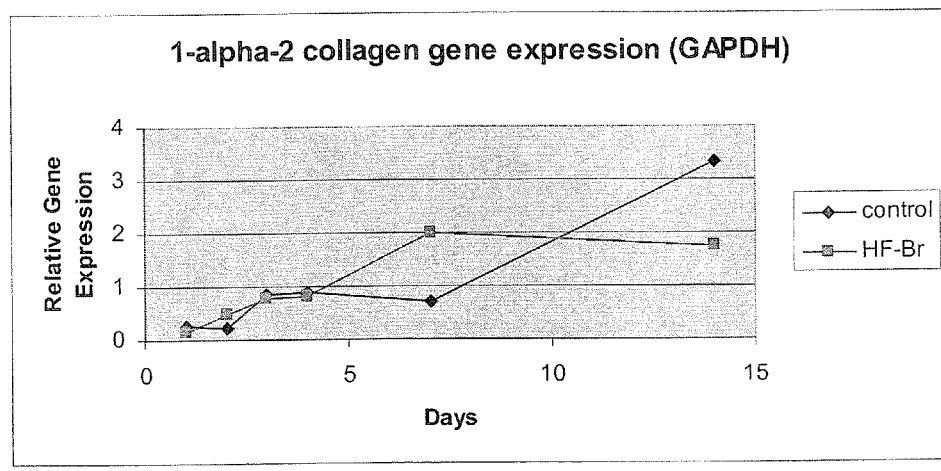

To determine alpha 1 collagen gene expression (in suture only animals), 2 mm punch biopsies of skin were taken at the border of wounds adjacent to suture material. Samples were flash frozen, pulverized, and RNA was extracted with Trizol reagent. Real time qPCR was employed to measure gene expression using rat 1-alpha-2 collagen ampliset. Relative quantities of alpha 1 collagen gene expression were normalized with expression levels of 18 S and GAPDH RNA. These values were then divided by the relative quantity of alpha 1 collagen gene expression in normal skin. Results showed that 1-alpha-2 collagen gene expression is inhibited in wounds treated topically with HF (FIG. 5).

Figure 6:
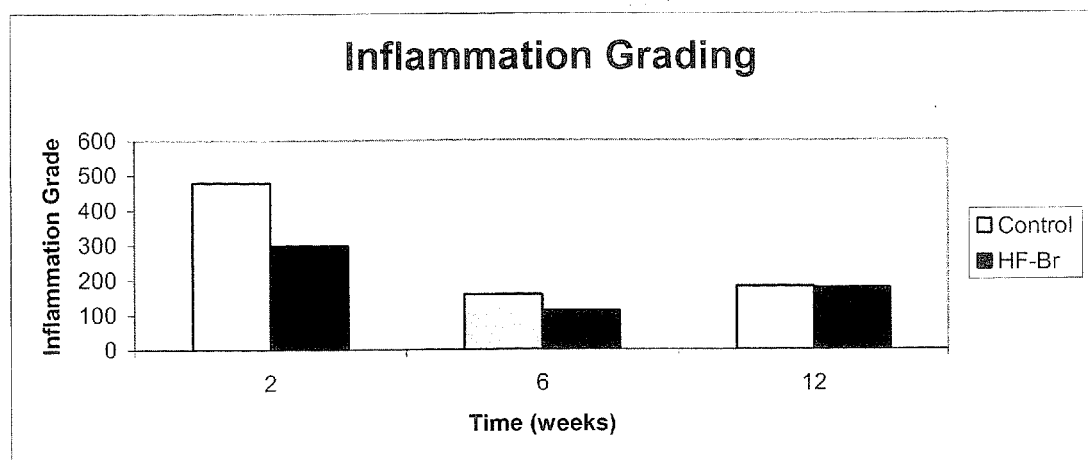
FIG. 6. Inflammation grading for weeks 2, 6 and 12.

The inflammatory response was visualized with H&E staining (not shown) and inflammation scores were consistently lower in HF—Br treated samples than in controls (FIG. 6). Masson's trichrome staining showed that cross sectional areas of collagen deposition (scar) were also consistently smaller in HF—Br treated samples than in controls (not shown).

Figure 7:
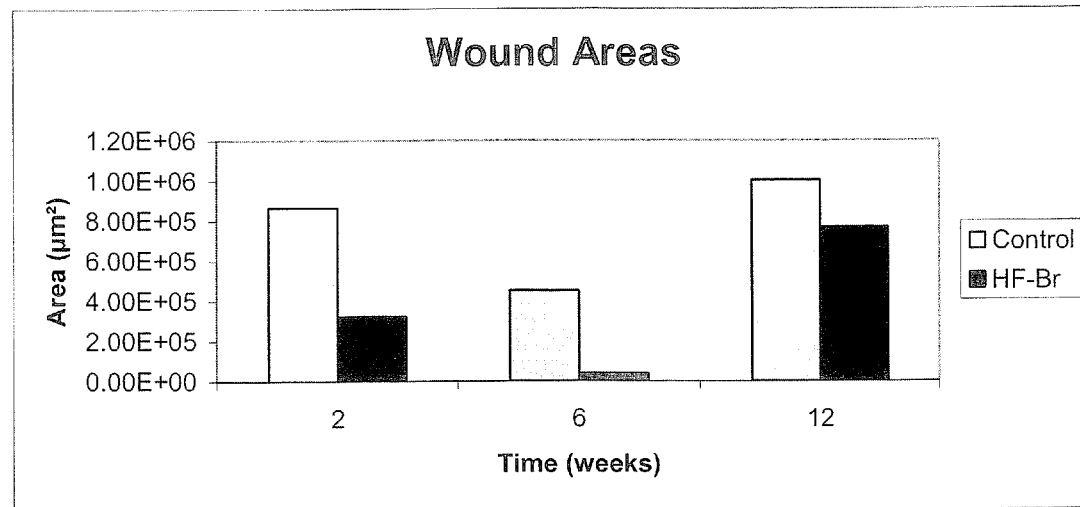
FIG. 7. Wound areas for weeks 2, 6 and 12.

Wound area approximations of Week 2 showed a 2.7 fold difference in collagen staining between HF—Br treated (322,107 μm²) and control (865,743 μm²) (not shown). Wound areas for weeks 2, 6 and 12 are shown in FIG. 7.

Figure 8:
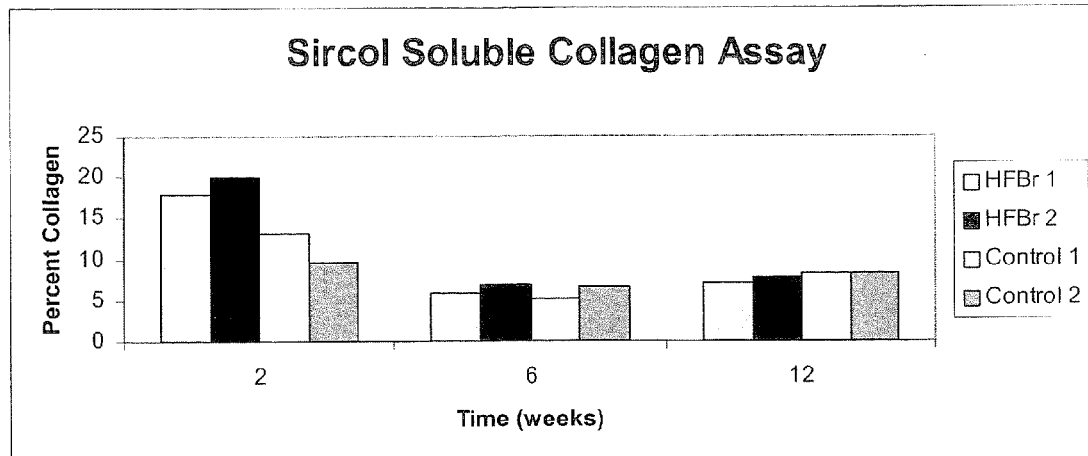
FIG. 8. Percent masses of salt soluble collagen in HF—Br treated and control wounds was determined by the Sircol™ Soluble Collagen Assay. Salt soluble collagen is representative of newly formed collagen.

To evaluate levels of newly formed collagen, tissue samples were digested in 1M NaCl in 0.05M Tris. Salt soluble collagen was then bound with a Sircol™ dye detection system and content was measured with UV spectrophotometry at 243 nm. Percent tissue masses of salt soluble collagen were higher in all week 2 samples. No significant difference in salt soluble collagen levels could be detected between HF—Br treated and control samples over each time point (FIG. 8).

Tensile strength of dermal would tissue specimens is assessed by measuring the breaking point with a tensometer. Tissue specimens are harvested and analyzed immediately after animals are sacrificed. The specimens are attached to the tensometer and pressure is applied until the wound breaks. This breaking pressure is recorded as tensile strength.

Figure 9A:
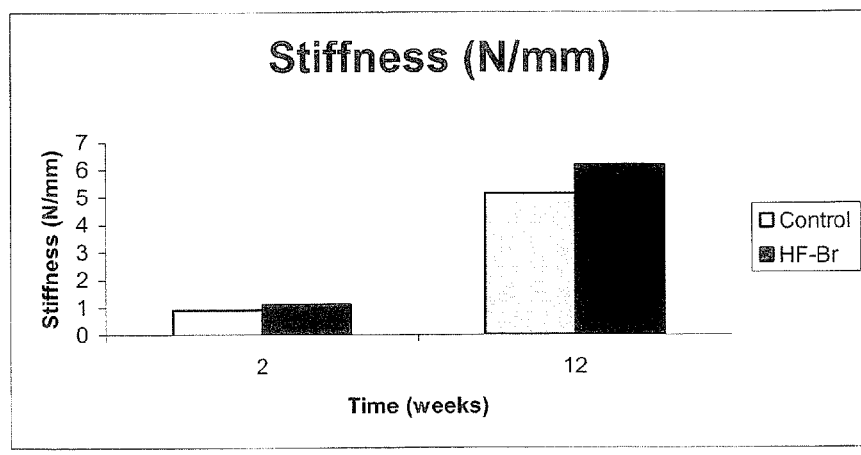
FIG. 9. Stiffness (9A), Ultimate Tensile Load (9B) and % Elongation (9C) of samples at 2 and 12 weeks.
Figure 9B:
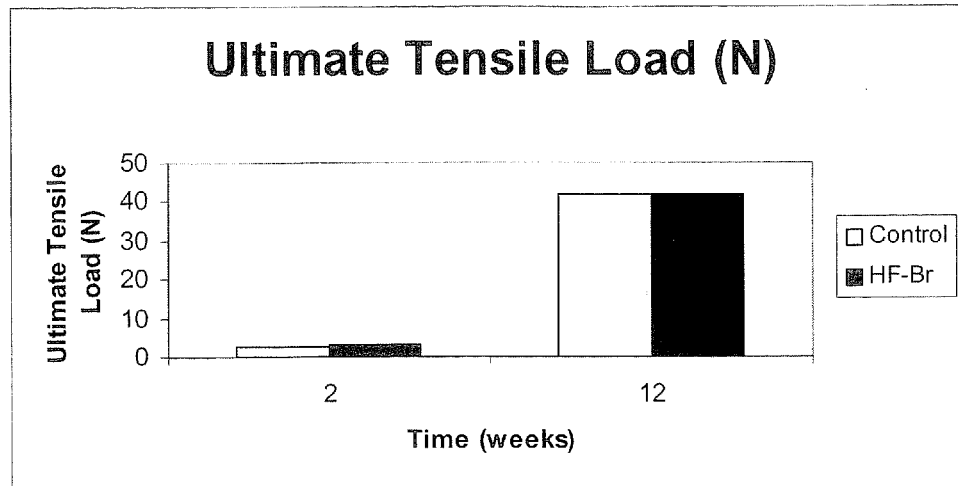
Figure 9C:
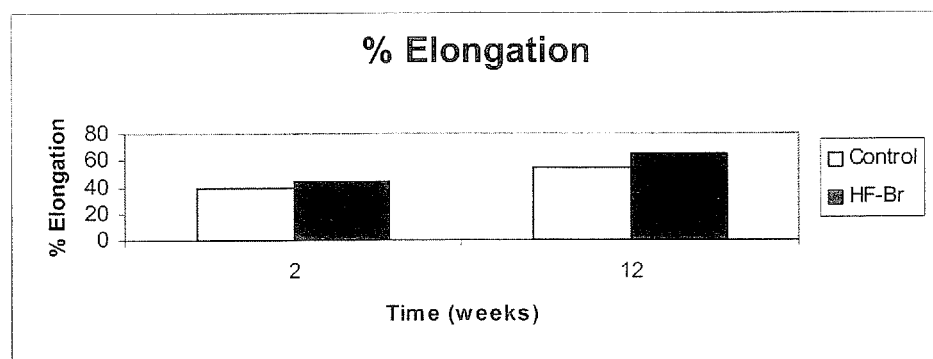

Skin samples were harvested so that the plane of the scar would be perpendicular to the direction of force applied. Samples were frozen, re-thawed, and secured by clamps in an tensometer (Instron™ Norwood, Mass.). Force was then applied until samples broke. Ultimate tensile load, percent elongation, and stiffness were then calculated for three control and three HF—Br treated samples at 2 and 12 weeks. Averages were reported. Average stiffness, ultimate tensile load, and percent elongation for all tissue samples increased from 2 to 12 weeks (FIG. 9). No significant difference was detected between treatment and control samples.

Conclusions: HF—Br coated suture delivers drug topically to dermal wounds, reducing scar tissue formation while maintaining tensile strength relative to control wounds. Type 1 Collagen content was the same in control and experimental wounds. HF can also be applied topically in the form of a cyanoacrylate based wound glue for effective wound closure.

Example 2

Paranasal Sinus Packing

The ability of halofuginone bromide (HF—Br), an inhibitor of the alpha-1 collagen gene, to prevent scar tissue formation was examined in a rodent model of paranasal sinus surgery. Systemic administration of this compound has been found to inhibit scar tissue formation in animal and human studies, though none have examined its effects on scar tissue formation in sinonasal surgery. It was the objective of this study to determine if topical application of HF—Br will prevent scarring in an animal model of paranasal sinus surgery.

The potency of halofuginone bromide has led us to hypothesize that topical application in low doses would be more than sufficient to inhibit collagen type-1 production in an open wound and would have virtually no systemic risk of side effects. Based upon this hypothesis, we have compounded a formulation of halofuginone bromide that can be used topically as a packing material in the sinus to prevent post-operative scar tissue formation.

The use of rodent models in the study of paranasal sinus injury and wound healing has been established by previous studies in mice (Bomer et al. *Arch Otolaryngol Head Neck Surg.* 1998 November; 124(11):1227-32), but none have examined the role of halofuginone bromide in this context. We have developed a rat model of sinus surgery useful in the study of wound healing, in which micro CT evaluation and histological data confirmed removal of ethmoid tissue similar to that seen after sinus surgery in a human while sparing critical structures (data not shown).

Halofuginone is combined with a suitable material that will absorb blood and fluid to help with hemostasis and to act as a drug delivery vehicle. We have chosen a cellulose derivative for this purpose.

The packing materials were prepared as follows. step 1: prepare materials to desired size and shape for implantation. Cellulose sinus packing material (Merocel) was cut into 5 mm strips. step 2: prepare a solution of HFBr 0.5 µg/ml (Halocur® (Oral Halofuginone. 0.5 mg/mL), Intervet International BV of Norway). step 3: materials are then dipped and immediately frozen at −80F for 24 hours. step 4: frozen materials are then lyophilized (vacuum dried). step 5: materials are sterilized using ethylene oxide or gamma irradiation. Visual inspection of the coated Merocel demonstrated a yellow coating, providing further evidence that the yellow Halocur had adhered.

Topical application of a halofuginone/cellulose derivative packing was tested for the prevention of scar tissue formation in the paranasal sinuses of a rat. The paired, anatomically identical paranasal sinuses of the rat allow one side to serve as a control and the other to serve as experimental. The control sinus was packed with an uncoated cellulose derivative packing material (Merocel). The other (experimental) sinus cavity was packed with a halofuginone bromide coated cellulose derivative compound packing material. A second set of animals underwent paranasal sinus surgery and no packing material of any kind was placed. Both packing preparations provide adequate homeostasis and require removal, as in the human clinical scenario. The surgical wound was closed using absorbable subcuticular sutures. Sinus surgery was performed in the rat and packs placed for 5 days. Sinus specimens were harvested and analyzed.

Table 1 below represents the weight of drug on the Merocel packs that were placed in the rat sinuses. Dry mass is weight of pack prior to coating with drug. Wet mass represents weight of pack after coating with drug. Drug mass represents total amount of drug applied as a coating to pack. This figure is calculated by subtracting dry mass from wet mass. Mean drug mass is the average of drug masses 1-10, with standard deviation as shown.

TABLE 1

Mass of HFBr-coated Cellulose Derivative (Merocel) Sinus Pack

| Pack | Dry Mass (g) | Wet Mass (g) | Drug Mass (g) |
|---|---|---|---|
| 1 | 0.0243 | 0.0301 | 0.0058 |
| 2 | 0.0244 | 0.0309 | 0.0065 |
| 3 | 0.0276 | 0.037 | 0.0094 |
| 4 | 0.0253 | 0.0326 | 0.0073 |
| 5 | 0.0245 | 0.0351 | 0.0106 |
| 6 | 0.0264 | 0.0344 | 0.008 |
| 7 | 0.0246 | 0.0315 | 0.0069 |
| 8 | 0.0282 | 0.0347 | 0.0065 |
| 9 | 0.0266 | 0.0344 | 0.0078 |
| 10 | 0.0274 | 0.0397 | 0.0123 |
| | Mean Drug Mass (g) | | 0.00811 |
| | Standard Dev | | 0.00201 |

Figure 10:
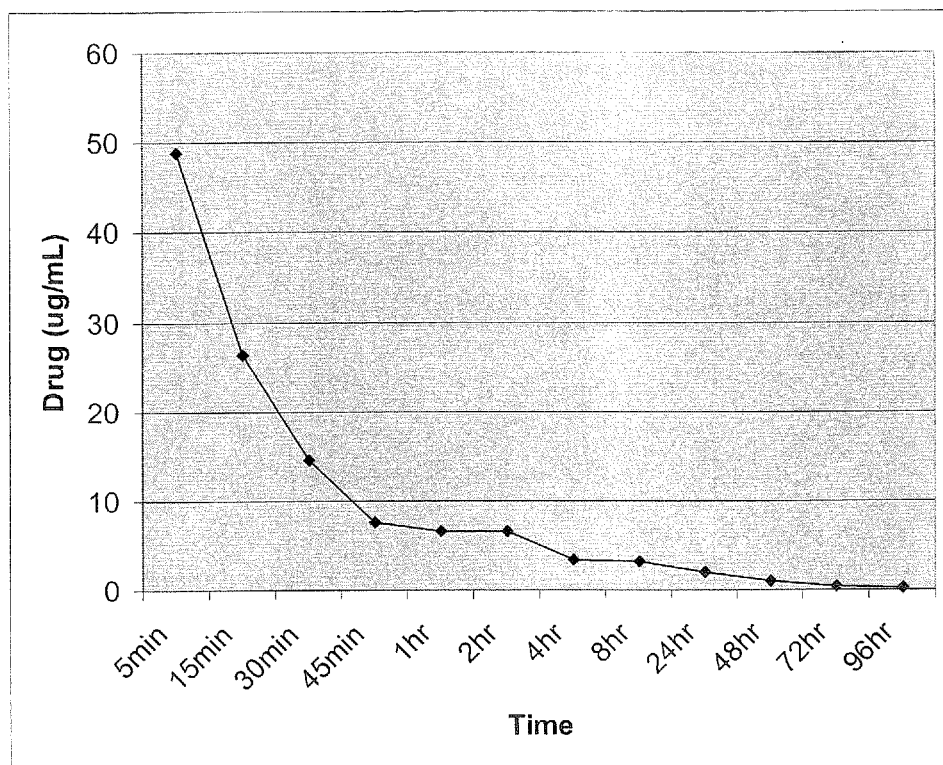
FIG. 10. Sinus Packing in vitro elution study. 80% of drug eluted in 1 hour.

Elution studies in vitro showed that 80% of the drug eluted in 1 hour (FIG. 10). In vivo elution studies were performed on packs removed 5 days post-operatively, placed in 10 mL PBS for 8 hrs, and 300 uL aliquot placed in spectrophotometer (blanked with a control pack removed post-operatively). No drug could be identified on post-op day 5 packing (not shown), suggesting that total amount of drug was given.

Figure 11:
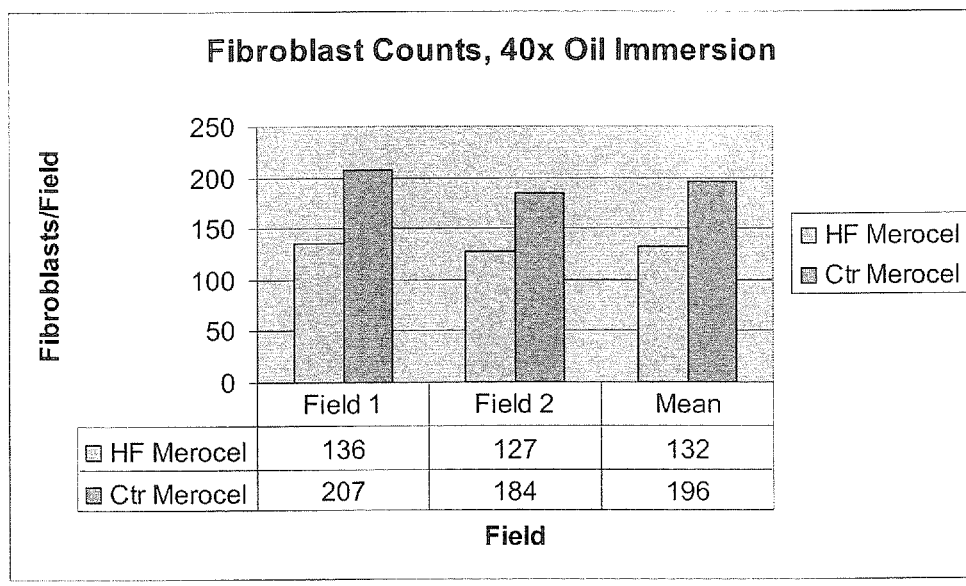
FIG. 11. Fibroblast Counts decreased in HF sinus pack wounds.

Fibroblast counts revealed decreased fibroblast counts in HF sinus pack wounds (FIG. 11). Collagen staining with Masson's trichrome staining showed decreased collagen staining in HF sinus pack wounds when compared to non-HF-coated cellulose pack (not shown).

Conclusions: Topical administration of HF—Br reduced post-operative scar formation in the paranasal sinus.

Example 3

Paranasal Sinus Packing Gel

An alternative to using a coated cellulose pack in the sinus is a sinus packing gel. This formulation was made by combining halofuginone (HF—Br) (Halocur® (Oral Halofuginone. 0.5 mg/mL), Intervet International BV of Norway) with carboxymethylcellulose (CMC) and storing as a sterile powder. The mixture is reconstituted with sterile water to form a gel and is then instilled in the sinus at the time of surgery for hemostasis and scar control.

Halofuginone in a liquid form is combined with a powder form of cellulose derivative to form an injectable gel. This gel is lyophilized and set aside for reconstitution with distilled water at the time of surgery. The amount of halofuginone present in the drug compound will be carefully controlled by weight and will represent 0.03% of the total compound dry weight.

Example 4

Treatment of Esophageal Stenosis with an Absorbable Drug Eluting Esophageal Stent Esophageal stenosis or stricture refers to narrowing of the esophagus secondary to the deposition of scar tissue in response to disruption of the epithelial lining. Deposition of scar tissue can occur secondary to gastroesophageal reflux disease (GERD), radiation or chemotherapy for cancer, surgery, trauma or inflammatory diseases. Contraction of this scar reduces the esophageal lumen, and can lead to the inability to swallow, inanition, aspiration and death (Ruigomez et al. *Am J Gastroenterol.* 2006; 101:2685-2692). When a tubular (luminal) structure is traumatized, the protective epithelial lining is disrupted and replaced by scar tissue that forms a circular scar. This circular scar contracts and reduces the luminal cross sectional area, which reduces flow through that structure.

Current treatments for luminal stricture conditions seek to stretch (dilate) and stent the involved segment of structured organ, to remove the involved segment of the organ, to bypass the involved organ or replace the organ entirely (organ transplant). The tissue trauma associated with these approaches inevitably leads to the formation of more scar tissue and an uninterrupted cycle of tissue trauma followed by scar tissue deposition, contraction and stenosis. Metallic stents have been used with limited success to try to resist contractile forces, but the chief drawback associated with this approach is that the stent causes continued tissue trauma that stimulates more collagen production and ultimately must be removed. For this reason, in some embodiments of the present invention, an absorbable stent is provided.

The gold standard, first line treatment for esophageal stricture disease has been endoscopic dilatation. Failure of such endoscopic procedures is common and necessitates a highly morbid open approach to remove the esophagus and reconstruct with gastric or free tissue transfer. The most common complication of either treatment is recurrence of stricture and need for repeat dilatation and stenting (Pereira-Lima et al. *Am J Gastroenterol.* 1999; 94:1497-1501).

Because of the poor success rate of operative approaches to esophageal stenosis, adjunctive surgical techniques have been employed to oppose the process of wound contraction and to prevent stricture recurrence. These methods include long term stenting with non-absorbable stents following stricture therapy as well as the local injection of various pharmacologic agents (corticosteroids, mitomycin C, colchicine, etc), in an effort to reduce the incidence of recurrence. None of these efforts have been successful and therefore a new treatment paradigm for dealing with this problem must be sought.

An absorbable esophageal stent is placed that administers topical collagen inhibitor after stricture lysis. These stents do not need to be removed, which minimizes risk to the patient. The drug eluting, absorbable esophageal stent will not only improve the treatment of esophageal stricture, but also have translational implications for treating other luminal strictures in anatomic sites such as the urethra, tracheobronchial tree, intestine, and blood vessels. There is evidence that orally administered or locally injected halofuginone can safely treat and prevent luminal stricture disease. Less is known about its effectiveness as a topical agent, but topical application is advantageous as it would deliver drug directly to tissue and it would avoid systemic doses which could interfere with systemic collagen homeostasis and blood coagulation. For example, in a recent Phase I clinical trial, systemic doses of 3.5 mg per day were associated with bleeding. Based upon this evidence, we believe that the ideal method of drug delivery would be topical on an absorbable, drug coated stent. Such a stent would administer drug directly to the area of injury with little or no systemic effect and the stent itself would be digested with no harmful effect.

Toward the goal of developing such a stent, investigators in Japan have recently showed promising results in a small human clinical trial in which an absorbable woven non-drug coated polylactic acid (PLA) stent was effective and safe for the treatment of benign esophageal stricture (Tanaka et al. *Digestion* 2006 October; 74:199-205).

We hypothesize that an absorbable HFBr coated esophageal stent will moderate scar tissue formation in a rat model of esophageal stricture formation, and we applied topical HF—Br in the form of an absorbable drug eluting esophageal stent in order to prevent cicatrization and luminal stenosis.

Previous animal models have used a caustic burn model (Sodium Hydroxide) to achieve esophageal injury. We were concerned that the pH of the esophagus would be sufficiently altered by sodium hydroxide so as to effectively alter the activity of a topical HFBr application and we therefore will use an electrocautery burn model.

Figure 12:
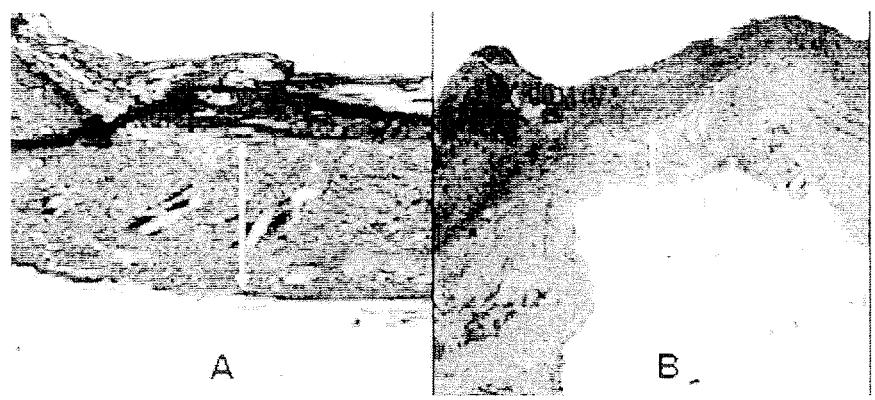
FIG. 12. A: Non-HFBr PLA implant (4×), B: HFBr electrospun implant (4×). Masson trichrome stain (blue is collagen). Note reduced thickness of collagen capsule (marked with arrows).

Electrospinning technology was used to make a polylactic acid (PLA)/HFBr impregnated material that we have implanted subcutaneously in a rat. We found that this material was readily absorbed with reduced fibrous (scar) capsule formation (FIG. 12). Electrospinning uses an electrical charge to form a mat of fine fibers. The standard setup for electrospinning consists of a spinneret with a metallic needle, a syringe pump, a high-voltage power supply, and a grounded collector. A polymer, sol-gel, composite solution (in our case PLA/HFBr melt solution) is loaded into the syringe and this liquid is driven to the needle tip by a syringe pump, forming a droplet at the tip. When a voltage is applied to the needle, the droplet is first stretched and then an electrified liquid jet is formed. The jet is then elongated and whipped continuously by electrostatic repulsion until it is deposited on the grounded collector. Whipping due to a bending instability in the electrified jet and concomitant evaporation of solvent allow this jet to be stretched to desired diameters.

For the esophageal stent we use this same procedure to spin a tubular structure that will have an outer diameter of 2.5-3 mm (the approximate diameter of an adult rat esophagus). We record the mass of PLA used and control the amount of drug used (0.5 mg maximum based on human data (de Jonge et al. *Eur J Cancer.* 2006 August; 42(12):1768-74) and our existing experience with HFBr in rats). Once the stent is fabricated, we study the material using scanning electron microscopy to look for even distribution of PLA and HFBr. We weigh and measure the length of each specimen and then perform drug elution studies in vitro as previously performed on paranasal sinus and suture materials. Briefly, we place the fabricated stent in PBS and measure drug levels using spectrophotometry at defined time points to establish a drug distribution (μg/ml) curve. Initially we measure time points of 5 min, 10 min, 20 min, 40 min, 60 min, 2 h, 4 h, 8 hr, 12 h 24 h 48 h 72 h and 96 h or until greater than 80% of drug has been released. These data allow us to estimate the amount of drug per unit length of stent.

The rat model described above is used to test our hypothesis that topical HFBr will inhibit scar tissue formation in the esophagus. Three groups of animals are used: Group 1 is normal rats, Group 2 is caustic esophageal injury without stent placement and Group 3 is caustic esophageal injury with PLA/HFBr stent placement. All animals undergo pre-operative weight, esophagram and serum blood draws for drug (HFBr) levels.

Animals in Groups 2 and 3 undergo surgery. In Group 3, the prefabricated stent is inserted through a small esophagotomy incision just distal to the burn injury at the time of burn injury and is secured with a single 6.0 monocryl suture to assure that the stent remains at the site of injury. The esophagotomy incision is closed with an interrupted absorbable suture. Wounds are closed in a standard fashion with absorbable suture, and animals are awakened and allowed to recover. In Group 3, 5 animals are euthanized at days 1, 2, 3, 4 and 5 for transcardiac serum blood draw to measure systemic levels of HFBr. In these same animals, the esophagus is opened and gross evaluation for stent integrity will be carried out. At 2, 6, 12 and 24 weeks remaining animals in all groups are weighed, euthanized and esophagram is performed. Esophageal specimens are harvested fixed in formalin, embedded in paraffin, sectioned and stained with hematoxylin and eosin and Masson's trichrome. We quantify the amount of scar tissue deposition using light microscopy and digital technology to measure scar areas. Real time PCR measurements are performed to quantify the activity of the Type-1α collagen activity. Pre and post weights are used as a marker of swallowing functionality and are compared across groups.

Example 5

Treatment of Abdominal Adhesions in a Rat Model

During surgery on large body cavities such as the abdomen, scar tissue forms and causes vital organs in that cavity to stick together in a process called adhesion formation. These adhesions cause loss of normal organ function and can lead to chronic pain and death. Prevention of adhesion formation would improve outcomes after surgery. Therefore one or more collagen inhibitors are topically applied to internal organs during or post surgery.

Adhesions are created in the abdominal cavity of animals are treated with a collagen inhibitor (e.g., halofuginone bromide) that blocks scar tissue formation. The drug is placed directly in the abdominal cavity by implanting an absorbable material or non-absorbable mesh in order to prevent adhesion formation between vital organs after surgery. The abdominal cavity is surgically opened and adhesions are created by gently rubbing the vital organs with a gauze sponge. Halofuginone bromide-coated absorbable hemostatic material is then applied directly into the abdominal cavity and the wounds are sewn shut.

The rat is used as the animal model. Experimental models for abdominal adhesion formation are well described in the rat and all incorporate ventral midline incisions. One incision is made on the abdomen of each rat and then a visceral abrasion is created to mimic human surgery. Separate control and experimental rats are used. In each experimental animal, a HF—Br coated absorbable material is implanted. In each control animal a non-HF—Br coated absorbable material is implanted. In a third control group no absorbable material is implanted. At 2, 6, 12 and 24 weeks, animals are euthanized, the amount of adhesion formation is quantified by percent area of adhesion formed in the abdominal wall, and the gross appearance of the adhesions is evaluated. Soft tissue specimens are harvested and analyzed for adhesion formation using hematoxylin and eosin staining, Masson's Trichrome staining and collagen content assay. Tensile strength of the abdominal wall is also measured at 12 weeks. On days 1, 2, 3, and 4, one rat from each experimental group is euthanized for intracardiac blood drawing to access plasma levels of HF—Br.

We have coated oxycellulose with HF—Br (not shown), and this is used as the packing material for the abdominal adhesion.

Example 6

Catheter Coating

The following is a list of ureteral and urethral catheter material that we have demonstrated the ability to coat with halofuginone using imaging studies (microscopic and gross), weight changes, and elution data over 4 days:

General device material: Silicone, Silastic, Latex, Polyurethane, Nitinol, PLGA.

Boston Scientific products: Percuflex stents, Flexima stents, Pebax material.

Cook stents: Polyurethane, Sof-flex, AQ stents, Endo-sof stents.

Bard stents: Polyurethane, Latex, Woven stents, Lubricath Foley, Inlay stent, Elastomer coated catheters, Silver coated catheters.

The stents were coated as follows: 1. Wet stent with PBS and cover with PBS soaked gauze and microwave for 40 sec; 2. Dip stent in 2% PLGA-COOH to cool; 3. Dry under hood; 4. Cover with PBS soaked gauze and microwave (or plasma) for 30 sec; 5. Coat stent with halofuginone (immerse) and freeze in liquid nitrogen and lyophilize overnight; 6. Weight should be measured before and after coating to estimate drug content.

Stents and other substrates made of the same materials (e.g., esophageal and tracheal products) are coated in the same fashion.

The foregoing is illustrative of the present invention, and is not to be construed as limiting thereof. The invention is defined by the following claims, with equivalents of the claims to be included therein.

That which is claimed is:

1. A wound closure device comprising a substrate and a collagen inhibitor on or in said substrate,
   wherein said collagen inhibitor is selected from the group consisting of: halofuginone and analogs thereof, and
   wherein said device is configured to substantially elute said collagen inhibitor over a period of up to 3 hours.

2. The device of claim 1, wherein said substrate is selected from the group consisting of biodegradable substrates and non-biodegradable (inert) substrates.

3. The device of claim 1, wherein said device is a suture, staple, tape, or bandage.

4. The device of claim 1, wherein said substrate comprises a biodegradable polymer.

5. The device of claim 1, wherein said substrate comprises a biodegradable polymer selected from the group consisting of poly(lactide)s, poly(glycolide)s, poly(lactide-coglycolide)s, poly(lactic acid)s, poly(glycolic acid)s, poly(lactic acid-co-glycolic acid)s, poly(caprolactone), polycarbonates, polyesteramides, polyanhydrides, poly(amino acid)s, poly(ortho ester)s, polycyanoacrylates, polyamides, polyacetals, poly(ether ester)s, copolymers of poly(ethylene glycol) and poly(ortho ester)s, poly(dioxanone)s, poly(alkylene alkylate)s, biodegradable polyurethanes, and blends and copolymers thereof.

6. The device of claim 1, wherein said device is a suture formed of braided, woven, or non-woven fiber material.

7. The device of claim 6, wherein said fiber material is silk, cotton, rayon, linen, wool, satin, nylon, polyester, polypropylene, polytetrafluoroethylene or a combination thereof.

8. A kit comprising:
(a) a wound closure device comprising a substrate coated with a collagen inhibitor; and
(b) a container in which said device is packaged in sterile form, wherein said collagen inhibitor is selected from the group consisting of: halofuginone and analogs thereof, and
wherein said device is configured to substantially elute said collagen inhibitor over a period of up to 3 hours.

9. The kit of claim 8, wherein said container comprises a plastic or foil container.

10. The kit of claim 8, wherein said container is vacuum-packed.

11. The kit of claim 8, wherein said substrate is coated with a single unit dose of said collagen inhibitor.

12. The kit of claim 8, wherein said substrate is biodegradable or non-biodegradable.

13. The kit of claim 8, wherein said device is a suture, staple, tape, or bandage.

14. The kit of claim 8, wherein said device is a suture formed of braided, woven, or non-woven fiber material.

15. The kit of claim 8, wherein said substrate is fiber material selected from: silk, cotton, rayon, linen, wool, satin, nylon, polyester, polypropylene, polytetrafluoroethylene, and a combination thereof.

16. The kit of claim 8, wherein said substrate comprises a biodegradable polymer.

17. The kit of claim 8, wherein said substrate comprises a biodegradable polymer selected from the group consisting of poly(lactide)s, poly(glycolide)s, poly(lactide-coglycolide)s, poly(lactic acid)s, poly(glycolic acid)s, poly(lactic acid-co-glycolic acid)s, poly(caprolactone), polycarbonates, polyesteramides, polyanhydrides, poly(amino acid)s, poly(ortho ester)s, polycyanoacrylates, polyamides, polyacetals, poly(ether ester)s, copolymers of poly(ethylene glycol) and poly(ortho ester)s, poly(dioxanone)s, poly(alkylene alkylate)s, biodegradable polyurethanes, and blends and copolymers thereof.

18. The device of claim 1, wherein said collagen inhibitor comprises halofuginone.

19. The kit of claim 8, wherein said collagen inhibitor comprises halofuginone.

20. The device of claim 1, wherein said device is a suture.

21. The device of claim 1, wherein said device is a staple.

22. The device of claim 1, wherein said device is a tape.

23. The device of claim 1, wherein said device is a bandage.

24. A wound closure device selected from the group consisting of: a suture, staple, tape, or bandage, said device comprising a substrate and a collagen inhibitor on or in said substrate,
wherein said collagen inhibitor is selected from the group consisting of: halofuginone and analogs thereof, and
wherein said device is configured to substantially elute said collagen inhibitor over a period of up to 2 hours.

25. The device of claim 24, wherein said substrate comprises a biodegradable polymer.

26. The device of claim 24, wherein said substrate comprises a biodegradable polymer selected from the group consisting of poly(lactide)s, poly(glycolide)s, poly(lactide-coglycolide)s, poly(lactic acid)s, poly(glycolic acid)s, poly(lactic acid-co-glycolic acid)s, poly(caprolactone), polycarbonates, polyesteramides, polyanhydrides, poly(amino acid)s, poly(ortho ester)s, polycyanoacrylates, polyamides, polyacetals, poly(ether ester)s, copolymers of poly(ethylene glycol) and poly(ortho ester)s, poly(dioxanone)s, poly(alkylene alkylate)s, biodegradable polyurethanes, and blends and copolymers thereof.

27. The device of claim 24, wherein said device is a suture.

28. The device of claim 24, wherein said device is a staple.

29. The device of claim 24, wherein said device is a tape.

30. The device of claim 24, wherein said device is a bandage.

31. The device of claim 24, wherein said device is configured to substantially elute said collagen inhibitor over a period of one hour.

32. The device of claim 24, wherein said device is configured to substantially elute said collagen inhibitor over a period of 30 minutes.

33. The device of claim 24, wherein said collagen inhibitor is halofuginone.

* * * * *

UNITED STATES PATENT AND TRADEMARK OFFICE
CERTIFICATE OF CORRECTION

PATENT NO.        : 8,668,703 B2                                              Page 1 of 1
APPLICATION NO.   : 11/948294
DATED             : March 11, 2014
INVENTOR(S)       : Sullivan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 644 days.

Signed and Sealed this
Thirtieth Day of May, 2017

Michelle K. Lee
*Director of the United States Patent and Trademark Office*

UNITED STATES PATENT AND TRADEMARK OFFICE
CERTIFICATE OF CORRECTION

PATENT NO. : 8,668,703 B2  
APPLICATION NO. : 11/948294  
DATED : March 11, 2014  
INVENTOR(S) : Sullivan et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 664 days.

Signed and Sealed this  
Sixth Day of December, 2022

Katherine Kelly Vidal  
*Director of the United States Patent and Trademark Office*